(12) United States Patent
Alarcon et al.

(10) Patent No.: US 11,206,868 B2
(45) Date of Patent: Dec. 28, 2021

(54) REFILLABLE ELECTRONIC CIGARETTE CLEAROMIZER

(71) Applicant: Fontem Holdings 1 B.V., Amsterdam (NL)

(72) Inventors: Ramon Alarcon, Los Gatos, CA (US); Dennis Rasmussen, Campbell, CA (US)

(73) Assignee: Fontem Holdings 1 B.V., Amsterdam (NL)

( * ) Notice: Subject to any disclaimer, the term of this patent is extended or adjusted under 35 U.S.C. 154(b) by 399 days.

(21) Appl. No.: 15/985,109

(22) Filed: May 21, 2018

(65) Prior Publication Data
US 2018/0310625 A1    Nov. 1, 2018

Related U.S. Application Data

(63) Continuation of application No. 15/219,161, filed on Jul. 25, 2016, now Pat. No. 9,993,025.

(51) Int. Cl.
| | |
|---|---|
| *A24F 11/00* | (2006.01) |
| *A24F 40/42* | (2020.01) |
| *H05B 3/03* | (2006.01) |
| *A24F 15/015* | (2020.01) |
| *A24F 40/10* | (2020.01) |
| *A24F 40/485* | (2020.01) |
| *F16K 17/02* | (2006.01) |
| *F16K 24/06* | (2006.01) |

(52) U.S. Cl.
CPC ............... *A24F 40/42* (2020.01); *H05B 3/03* (2013.01); *A24F 15/015* (2020.01); *A24F 40/10* (2020.01); *A24F 40/485* (2020.01); *A61M 2209/045* (2013.01); *F16K 17/02* (2013.01); *F16K 24/06* (2013.01)

(58) Field of Classification Search
CPC ......... A24F 11/00; A24F 25/02; A24F 47/008
See application file for complete search history.

(56) References Cited

U.S. PATENT DOCUMENTS

| | | |
|---|---|---|
| 3,482,580 A | 12/1969 | Hollabaugh |
| 4,637,407 A | 1/1987 | Bonanno |

(Continued)

FOREIGN PATENT DOCUMENTS

| | | |
|---|---|---|
| CN | 103653244 A | 3/2014 |
| CN | 103653246 A | 3/2014 |

(Continued)

OTHER PUBLICATIONS

Shenzen IVPS Technology Co., Ltd.; TF-RTA Rebuildable Tank Atomizer. http://www.smoktech.com/atomizer/tf-rta; Shenzen, CN.

(Continued)

*Primary Examiner* — Thanh Tam T Le
(74) *Attorney, Agent, or Firm* — Dykema Gossett PLLC

(57) ABSTRACT

Aspects of the instant disclosure relate to electronic cigarettes; more particularly, to electronic cigarettes including a clearomizer. Various embodiments of the present disclosure are directed to a clearomizer with a refillable electronic cigarette juice tank with a first fill aperture, and a mouthpiece including a second fill aperture. The mouthpiece and the refillable tank rotate relative to one another along a common longitudinal axis to align the fill apertures, and facilitate filling of the refillable tank.

17 Claims, 5 Drawing Sheets

(56) References Cited

U.S. PATENT DOCUMENTS

| | | | |
|---|---|---|---|
| 4,735,217 A | 4/1988 | Gerth | |
| 4,776,353 A | 10/1988 | Lilja | |
| 4,945,929 A * | 8/1990 | Egilmex | A61M 15/06 |
| | | | 131/273 |
| 7,530,357 B2 | 5/2009 | Edwards, Jr. | |
| 7,997,280 B2 | 8/2011 | Rosenthal | |
| 8,383,331 B2 | 3/2013 | Hon | |
| 8,511,318 B2 * | 8/2013 | Hon | A61K 9/007 |
| | | | 131/273 |
| 8,528,569 B1 * | 9/2013 | Newton | A24F 40/42 |
| | | | 131/194 |
| 8,794,231 B2 | 8/2014 | Thorens et al. | |
| 8,903,228 B2 * | 12/2014 | Goodman | F22B 1/282 |
| | | | 131/330 |
| 8,991,402 B2 * | 3/2015 | Bowen | A61M 11/041 |
| | | | 131/194 |
| 9,399,110 B2 | 7/2016 | Goodman | |
| 9,572,374 B2 * | 2/2017 | Gabbay | A24F 40/485 |
| 9,993,025 B2 * | 6/2018 | Alarcon | A24F 47/008 |
| 2004/0237974 A1 | 12/2004 | Min | |
| 2005/0016550 A1 * | 1/2005 | Katase | A61M 11/005 |
| | | | 131/194 |
| 2005/0268911 A1 * | 12/2005 | Cross | A61M 15/0045 |
| | | | 128/204.17 |
| 2006/0196518 A1 * | 9/2006 | Hon | A61K 9/007 |
| | | | 131/360 |
| 2009/0095287 A1 * | 4/2009 | Emarlou | A61M 11/041 |
| | | | 128/200.14 |
| 2011/0232654 A1 | 9/2011 | Mass | |
| 2014/0123989 A1 | 5/2014 | LaMothe | |
| 2014/0190503 A1 | 7/2014 | Li et al. | |
| 2015/0144145 A1 | 5/2015 | Chang et al. | |
| 2015/0257447 A1 | 9/2015 | Sullivan | |
| 2015/0305409 A1 | 10/2015 | Verleur | |
| 2015/0335075 A1 * | 11/2015 | Minskoff | A24F 47/008 |
| | | | 131/329 |
| 2016/0007654 A1 * | 1/2016 | Zhu | A24F 47/008 |
| | | | 131/328 |
| 2016/0191546 A1 | 6/2016 | Spikes | |
| 2016/0198767 A1 * | 7/2016 | Verleur | H05B 1/0202 |
| | | | 392/386 |
| 2016/0227837 A1 | 8/2016 | Hammel | |
| 2016/0235121 A1 | 8/2016 | Rogan et al. | |
| 2016/0332754 A1 | 11/2016 | Brown | |

FOREIGN PATENT DOCUMENTS

| | | |
|---|---|---|
| CN | 203633507 U | 6/2014 |
| CN | 105212279 A | 1/2016 |
| CN | 205143487 U | 4/2016 |
| EP | 2823720 A1 | 6/2014 |
| EP | 3031339 A1 | 6/2016 |
| GB | 2531830 A | 5/2017 |
| WO | 2016096337 A1 | 6/2016 |
| WO | 2016124717 A1 | 8/2016 |

OTHER PUBLICATIONS

Shenzen IVPS Technology Co., Ltd.; Stick One Kit—SMOK®. http://www.smoktech.com/kit/stick-one-kit; Shenzen, CN.
Tobeco Technology; Guide to Vaping; Tobeco TurboV3 RDA; http://guidetovaping.com/2015/08/17/tobeco-hits-the-market-with-the-turbo-v3-rda/.
Advken; Mad Hatter RDA; http://www.advken.com/atomizer/mad-hatter-rda.html.

\* cited by examiner

REFILLABLE ELECTRONIC CIGARETTE CLEAROMIZER

CROSS-REFERENCE TO RELATED APPLICATION

This application is a continuation of U.S. patent application Ser. No. 15/219,161 entitled "REFILLABLE ELECTRONIC CIGARETTE CLEAROMIZER," filed 25 Jul. 2016, now pending, which is hereby incorporated by reference as though fully set forth herein.

BACKGROUND a. Field

The instant disclosure relates to an electronic cigarette; and more particularly to a refillable clearomizer for an electronic cigarette.

b. Background Art

Electronic cigarettes, also known as e-cigarette (eCigs) and personal vaporizers (PVs), are electronic inhalers that vaporize or atomize a liquid solution into an aerosol mist that may then be delivered to a user. A typical eCig has two main parts—a power supply portion and a atomizer/liquid reservoir portion (which may be a clearomizer). The battery part typically includes a rechargeable lithium-ion (Li-ion) battery, a light emitting diode (LED), and a pressure sensor. The clearomizer typically includes a refillable liquid solution tank, an atomizer and a mouthpiece. The atomizer typically includes a heating coil that vaporizes the liquid solution.

The foregoing discussion is intended only to illustrate the present field and should not be taken as a disavowal of claim scope.

BRIEF SUMMARY

In one embodiment of the present disclosure, an eCig clearomizer is disclosed. The eCig clearomizer including a refillable eCig juice tank.

Various embodiments of the present disclosure are directed to an eCig clearomizer including a refillable tank and a mouthpiece. The refillable tank including a tank proximal portion and a tank distal portion, a first fill aperture, and a first annular channel around the proximal portion of the tank. The mouthpiece including a mouthpiece proximal portion and a mouthpiece distal portion, a second fill aperture, a first annular protuberance around the distal portion of the mouthpiece, wherein the first annular protuberance is slidably retained in the first annular channel to facilitate rotation of the mouthpiece relative to the refillable tank.

Aspects of the present disclosure are also directed toward an eCig clearomizer including a refillable tank, a heater coil, a wick, and a mouthpiece. The refillable tank is designed to contain eCig juice, which is drawn from the refillable tank to the heater coil by capillary action, where the heater coil atomizes the eCig juice in response to a current draw across the heater coil. The mouthpiece is coupled to a proximal portion of the refillable tank, and rotates relative to the refillable tank along a common longitudinal axis of the refillable tank and the mouthpiece.

In yet other embodiments, an eCig clearomizer is disclosed including a hemicylindrical port. The port includes a fluid inlet, and three electrical pads. At least one of the electrical pads are electrically coupled to a heater coil within the clearomizer, and the port electrically couples the heater coil with electrical circuitry of a power supply portion. The port also transfers a fluid from the power supply portion to the clearomizer, via the fluid inlet, in response to a draw.

Additional features, advantages, and embodiments of the disclosure may be set forth or apparent from consideration of the detailed description and drawings. Moreover, it is to be understood that the foregoing summary of the disclosure and the following detailed description and drawings are exemplary and intended to provide further explanation without limiting the scope of the disclosure as claimed.

BRIEF DESCRIPTION OF THE DRAWINGS

Various example embodiments may be more completely understood in consideration of the following detailed description in connection with the accompanying drawings.

Figure 1:
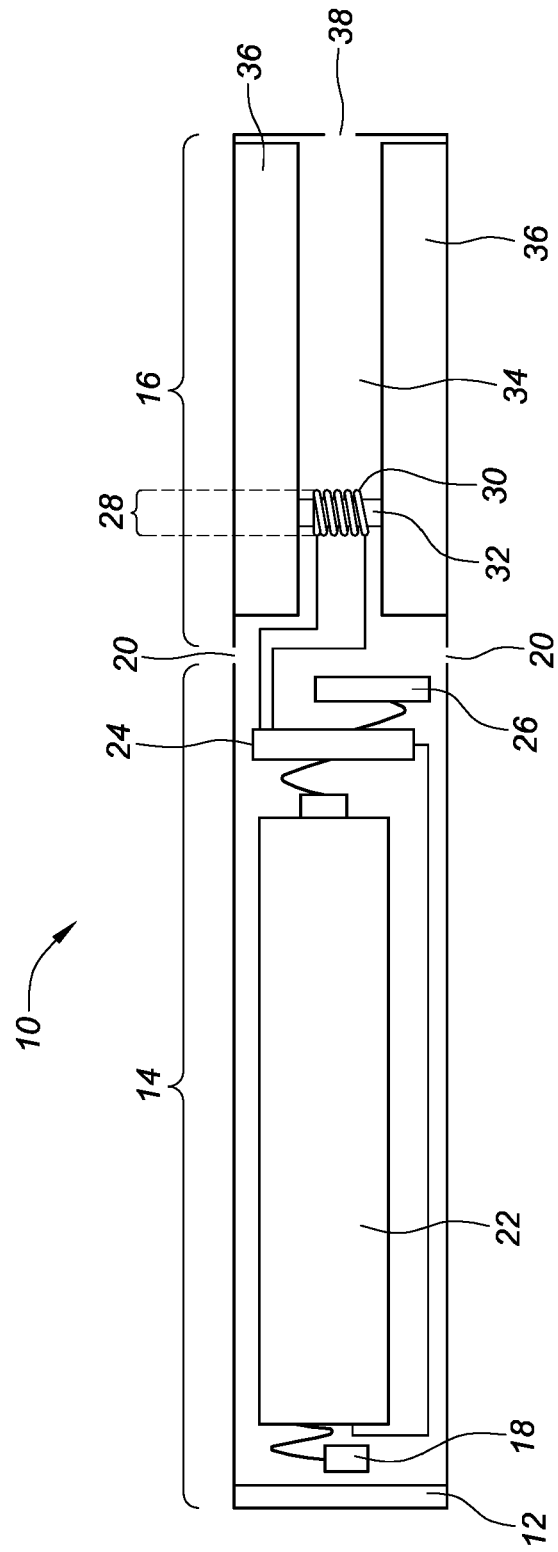
FIG. 1 is a cross-sectional side view of an eCig, consistent with various aspects of the present disclosure.

While various embodiments discussed herein are amenable to modifications and alternative forms, aspects thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims.

DETAILED DESCRIPTION OF EMBODIMENTS

The disclosure and the various features and advantageous details thereof are explained more fully with reference to the non-limiting embodiments and examples that are described and/or illustrated in the accompanying drawings and detailed in the following.

Throughout the following, an electronic smoking device will be exemplarily described with reference to an e-cigarette. As is shown in FIG. 1, an e-cigarette 10 typically has a housing comprising a cylindrical hollow tube having an end cap 12. The cylindrical hollow tube may be a single-piece or a multiple-piece tube. In FIG. 1, the cylindrical hollow tube is shown as a two-piece structure having a power supply portion 14 and an atomizer/liquid reservoir portion 16. Together the power supply portion 14 and the atomizer/liquid reservoir portion 16 form a cylindrical tube which can be approximately the same size and shape as a conventional cigarette, typically about 100 mm with a 7.5 mm diameter, although lengths may range from 70 to 150 or 180 mm, and diameters from 5 to 28 mm.

The power supply portion 14 and atomizer/liquid reservoir portion 16 are typically made of metal (e.g., steel or aluminum, or of hardwearing plastic) and act together with the end cap 12 to provide a housing to contain the components of the e-cigarette 10. The power supply portion 14 and the atomizer/liquid reservoir portion 16 may be configured to fit together by, for example, a friction push fit, a snap fit, a bayonet attachment, a magnetic fit, or screw threads. The end cap 12 is provided at the front end of the power supply portion 14. The end cap 12 may be made from translucent plastic or other translucent material to allow a light-emitting diode (LED) 18 positioned near the end cap to emit light through the end cap. Alternatively, the end cap may be made of metal or other materials that do not allow light to pass.

An air inlet may be provided in the end cap, at the edge of the inlet next to the cylindrical hollow tube, anywhere along the length of the cylindrical hollow tube, or at the connection of the power supply portion 14 and the atomizer/liquid reservoir portion 16. FIG. 1 shows a pair of air inlets 20 provided at the intersection between the power supply portion 14 and the atomizer/liquid reservoir portion 16.

A power supply, preferably a battery 22, the LED 18, control electronics 24 and, optionally, an airflow sensor 26 are provided within the cylindrical hollow tube power supply portion 14. The battery 22 is electrically connected to the control electronics 24, which are electrically connected to the LED 18 and the airflow sensor 26. In this example, the LED 18 is at the front end of the power supply portion 14, adjacent to the end cap 12; and the control electronics 24 and airflow sensor 26 are provided in the central cavity at the other end of the battery 22 adjacent the atomizer/liquid reservoir portion 16.

The airflow sensor 26 acts as a puff detector, detecting a user puffing or sucking on the atomizer/liquid reservoir portion 16 of the e-cigarette 10. The airflow sensor 26 can be any suitable sensor for detecting changes in airflow or air pressure, such as a microphone switch including a deformable membrane which is caused to move by variations in air pressure. Alternatively, the sensor may be, for example, a Hall element or an electro-mechanical sensor.

The control electronics 24 are also connected to an atomizer 28. In the example shown, the atomizer 28 includes a heating coil 30 which is wrapped around a wick 32 extending across a central passage 34 of the atomizer/liquid reservoir portion 16. The central passage 34 may, for example, be defined by one or more walls of the liquid reservoir and/or one or more walls of the atomizer/liquid reservoir portion 16 of the e cigarette 10. The coil 30 may be positioned anywhere in the atomizer 28 and may be transverse or parallel to a longitudinal axis of a cylindrical liquid reservoir 36. The wick 32 and heating coil 30 do not completely block the central passage 34. Rather an air gap is provided on either side of the heating coil 30 enabling air to flow past the heating coil 30 and the wick 32. The atomizer may alternatively use other forms of heating elements, such as ceramic heaters, or fiber or mesh material heaters. Nonresistance heating elements such as sonic, piezo, and jet spray may also be used in the atomizer in place of the heating coil.

The central passage 34 is surrounded by the cylindrical liquid reservoir 36 with the ends of the wick 32 abutting or extending into the liquid reservoir 36. The wick 32 may be a porous material such as a bundle of fiberglass fibers or cotton or bamboo yarn, with liquid in the liquid reservoir 36 drawn by capillary action from the ends of the wick 32 towards the central portion of the wick 32 encircled by the heating coil 30.

The liquid reservoir 36 may alternatively include wadding (not shown in FIG. 1) soaked in liquid which encircles the central passage 34 with the ends of the wick 32 abutting the wadding. In other embodiments, the liquid reservoir may comprise a toroidal cavity arranged to be filled with liquid and with the ends of the wick 32 extending into the toroidal cavity.

An air inhalation port 38 is provided at the back end of the atomizer/liquid reservoir portion 16 remote from the end cap 12. The inhalation port 38 may be formed from the cylindrical hollow tube atomizer/liquid reservoir portion 16 or may be formed in an end cap.

In use, a user sucks on the e-cigarette 10. This causes air to be drawn into the e cigarette 10 via one or more air inlets, such as air inlets 20, and to be drawn through the central passage 34 towards the air inhalation port 38. The change in air pressure which arises is detected by the airflow sensor 26, which generates an electrical signal that is passed to the control electronics 24. In response to the signal, the control electronics 24 activate the heating coil 30, which causes liquid present in the wick 32 to be vaporized creating an aerosol (which may comprise gaseous and liquid components) within the central passage 34. As the user continues to suck on the e-cigarette 10, this aerosol is drawn through the central passage 34 and inhaled by the user. At the same time, the control electronics 24 also activate the LED 18 causing the LED 18 to light up, which is visible via the translucent end cap 12. Activation of the LED may mimic the appearance of a glowing ember at the end of a conventional cigarette. As liquid present in the wick 32 is converted into an aerosol, more liquid is drawn into the wick 32 from the liquid reservoir 36 by capillary action and thus is available to be converted into an aerosol through subsequent activation of the heating coil 30.

Some e-cigarette are intended to be disposable and the electric power in the battery 22 is intended to be sufficient to vaporize the liquid contained within the liquid reservoir 36, after which the e-cigarette 10 is thrown away. In other embodiments, the battery 22 is rechargeable and the liquid reservoir 36 is refillable. In the cases where the liquid reservoir 36 is a toroidal cavity, this may be achieved by refilling the liquid reservoir 36 via a refill port (not shown in FIG. 1). In other embodiments, the atomizer/liquid reservoir portion 16 of the e cigarette 10 is detachable from the power supply portion 14 and a new atomizer/liquid reservoir portion 16 can be fitted with a new liquid reservoir 36 thereby replenishing the supply of liquid. In some cases, replacing the liquid reservoir 36 may involve replacement of the heating coil 30 and the wick 32 along with the replacement of the liquid reservoir 36. A replaceable unit comprising the atomizer 28 and the liquid reservoir 36 may be referred to as a cartomizer.

The new liquid reservoir may be in the form of a cartridge (not shown in FIG. 1) defining a passage (or multiple passages) through which a user inhales aerosol. In other embodiments, the aerosol may flow around the exterior of the cartridge to the air inhalation port 38.

Of course, in addition to the above description of the structure and function of a typical e cigarette 10, variations also exist. For example, the LED 18 may be omitted. The airflow sensor 26 may be placed, for example, adjacent to the end cap 12 rather than in the middle of the e-cigarette. The airflow sensor 26 may be replaced by, or supplemented with, a switch which enables a user to activate the e cigarette manually rather than in response to the detection of a change in airflow or air pressure.

Different types of atomizers may be used. Thus, for example, the atomizer may have a heating coil in a cavity in the interior of a porous body soaked in liquid. In this design, aerosol is generated by evaporating the liquid within the porous body either by activation of the coil heating the porous body or alternatively by the heated air passing over or through the porous body. Alternatively the atomizer may use a piezoelectric atomizer to create an aerosol either in combination or in the absence of a heater.

Figure 2A:
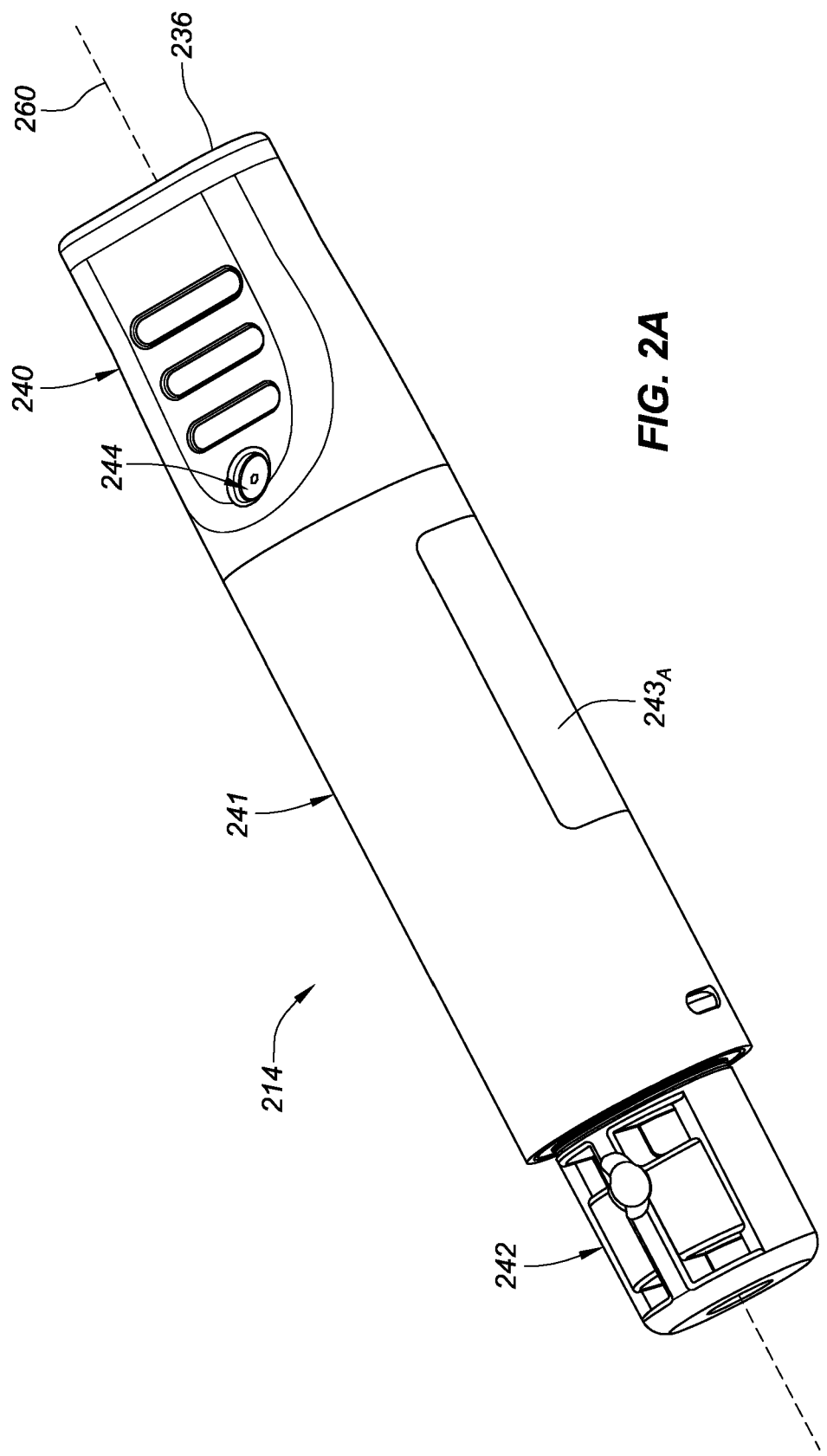
FIG. 2A is an isometric top view of a refillable eCig clearomizer, consistent with various aspects of the present disclosure.
Figure 2B:
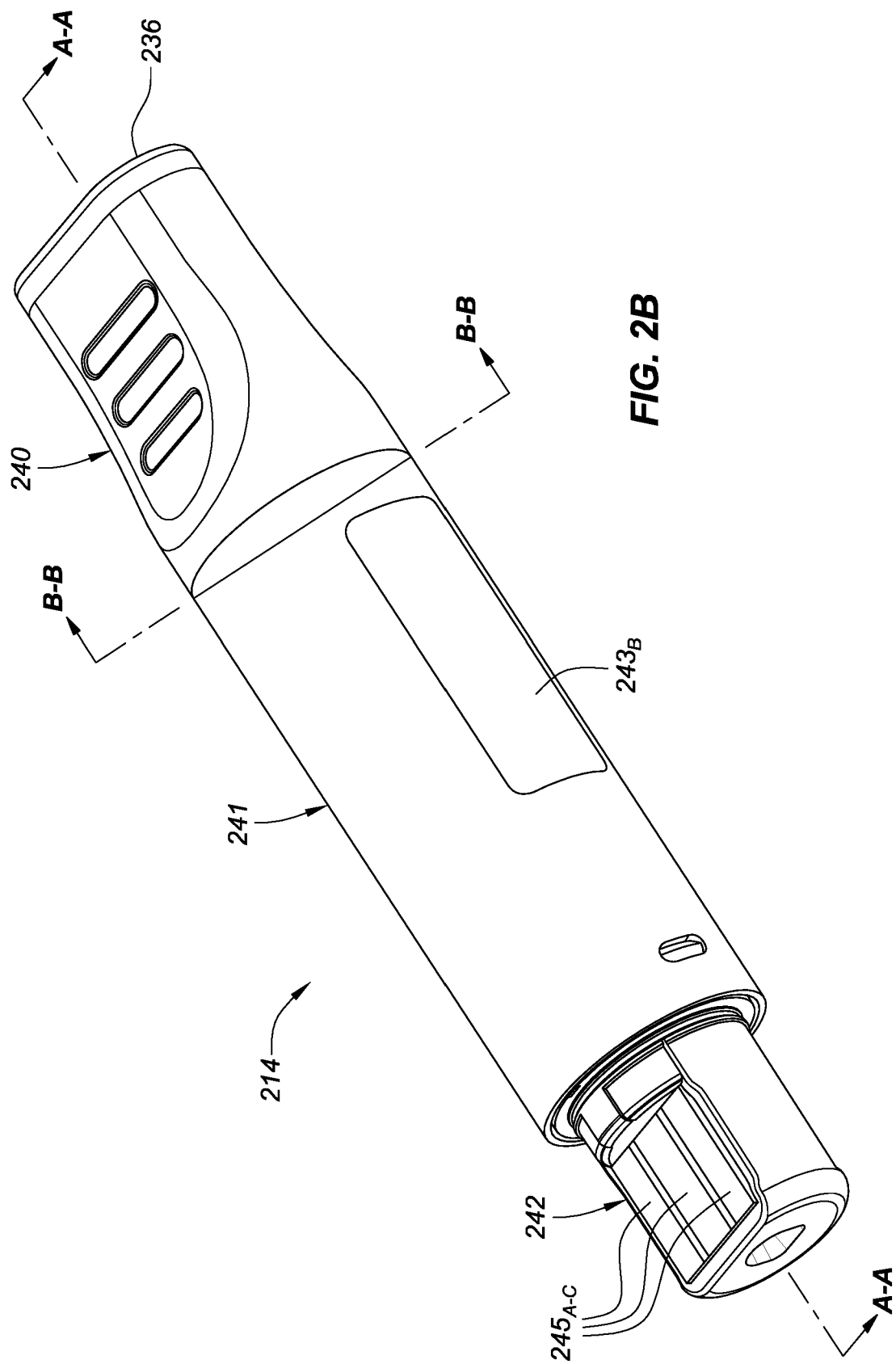
FIG. 2B is an isometric bottom view of the refillable eCig clearomizer of FIG. 2A, consistent with various aspects of the present disclosure.

FIG. 2A is an isometric top view of a refillable eCig clearomizer 214 and FIG. 2B is an isometric bottom view of the refillable eCig clearomizer 214 of FIG. 2A, consistent with various aspects of the present disclosure. As shown in FIGS. 2A-B, the clearomizer 214 consists of three portions—a mouthpiece 240, a refillable tank 241, and a hemicylindrical port 242. Hemicylindrical as user herein describes parts having the shape of a half cylinder, as well as parts that include a larger or smaller portion of a cylinder when cut by a plane that is parallel to the longitudinal (or lengthwise) axis of the cylinder. The port 242 mechanically couples the clearomizer 214 to a power supply portion, fluidly couples an airflow between the power supply portion and the clearomizer 214, and electrically couples power supply portion circuitry with a heater coil (and optionally a clearomizer memory circuit) within the clearomizer 214. The refillable tank portion 241 is designed to hold eCig juice. The amount of eCig juice within the refillable tank portion 241 may be visually determined by a user via one or more windows $243_{A-B}$. In one example embodiment, when the user holds the clearomizer 214 vertically, the user may be able to approximate the amount of eCig juice remaining in the refillable tank.

When in use, a user draws from a nozzle 236 in the mouthpiece portion 240 of the clearomizer 214. After a number of draws, the eCig juice within the refillable tank depletes and requires a refill before the user may continue to use the eCig. By rotating the mouthpiece 240 relative to the refillable tank portion 241, a filling port 244 may be exposed that provides access to the refillable tank for refilling with eCig juice. In various embodiments, the user may visually determine when to discontinue filling based on a level of eCig juice visually indicated by one or more windows $243_{A-B}$. Once filling is complete, the user may rotate the mouthpiece 240 relative to the refillable tank portion 241 to hide the filling port 244 and to recommence regular operation of the eCig.

In various embodiments of the present disclosure, a sensor within a power supply portion of the eCig may measure the flow of air into the clearomizer 214, in response to a user's draw. Based on the sensor signal, controller circuitry within the power supply portion may generate and transmit power signals to a heater coil within the clearomizer 214 via electrical pads $245_{A-C}$. In such an embodiment, the heater coil may receive a linear or non-linear power output based on a sensed airflow rate. In some embodiments, based on a sensed current across the heater coil, the controller circuitry within the power supply portion can determine a dry-state of a wick interfacing with the heater coil and disable the eCig until the refillable tank is refilled with eCig juice. Such an embodiment may prevent damage to the eCig, as well as improve user experience.

Figure 2C:
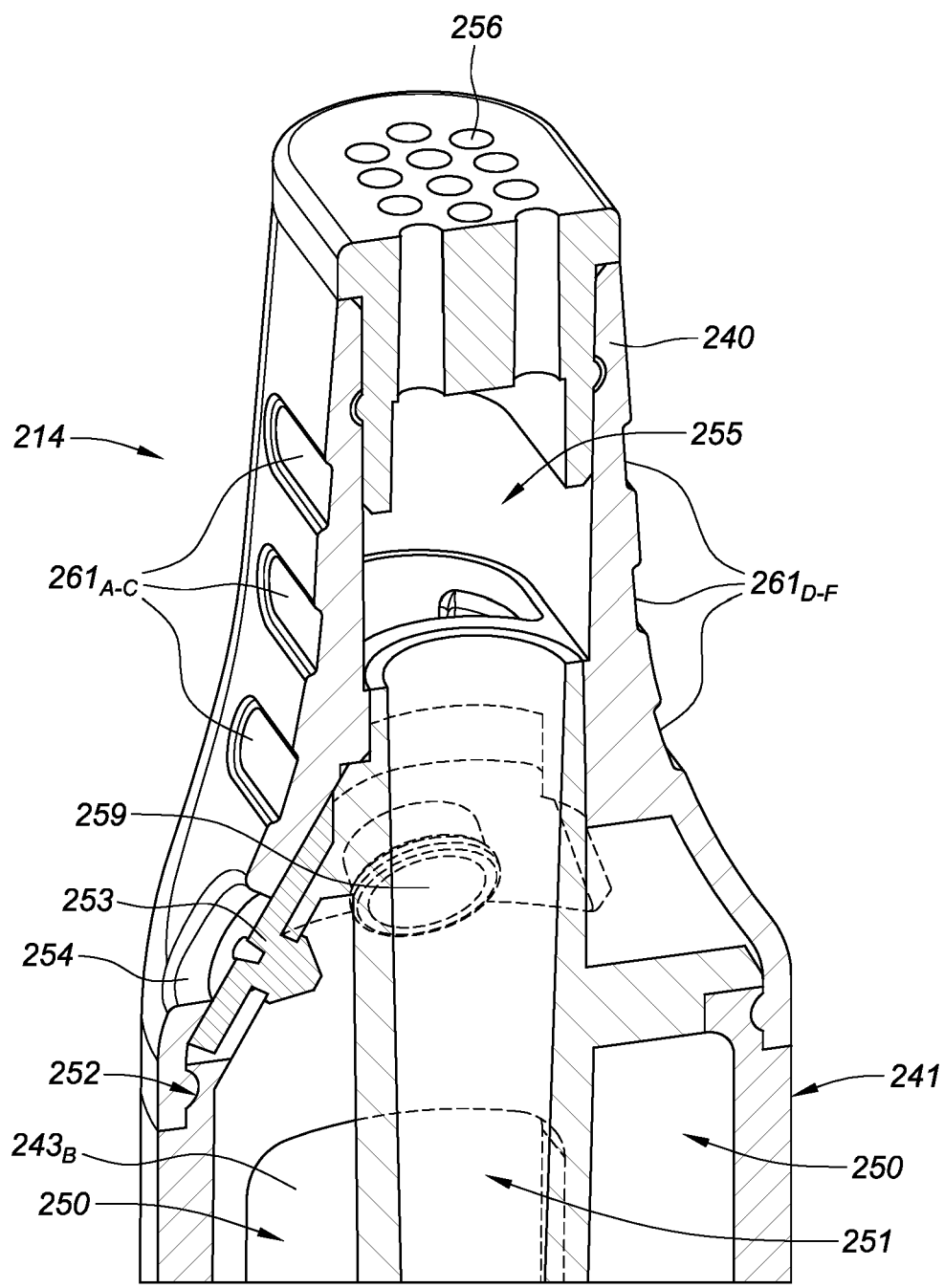
FIG. 2C is a partial cross-sectional view of the refillable eCig clearomizer taken along line A-A of FIG. 2B, consistent with various aspects of the present disclosure.

FIG. 2C is a cross sectional side view of the refillable eCig clearomizer 214 of FIG. 2A, consistent with various aspects of the present disclosure. As shown in FIG. 2C, a mouthpiece 240 and a refillable tank portion 241 of the clearomizer 214 have a mutual interface 252, along which the refillable tank portion and the mouthpiece rotate about a common longitudinal axis 260 (as shown in FIG. 2A).

A central passage 251 within clearomizer 214 delivers a flow of air with atomized eCig juice from a heater coil (not shown), through a vapor chamber 255 and a plurality of nozzle apertures 256, to the user.

When a refillable tank 250 within a refillable tank portion 241 of a clearomizer 214 is empty, a user may access the refillable tank and inject more eCig juice into the refillable tank 250 by manipulating the relationship between mouthpiece 240 and the refillable tank portion 241. Specifically, the mouthpiece 240 may be rotationally manipulated along an interface 252 between the mouthpiece and the refillable tank portion—aligning a first fill aperture 259 of the refillable tank portion with a second fill aperture 254 of the mouthpiece. When aligned, the first and second fill apertures facilitate introducing eCig juice into the refillable tank 250. The user may fill the clearomizer 214 with eCig juice, relying on a visual indication via windows $243_{A-B}$ to determine when to discontinue filling the tank.

Interface 252 may include an inwardly-facing annular protuberance of mouthpiece 240 which is captured in a complementary outwardly-facing annular channel of refillable tank portion 241, facilitating rotation of the mouthpiece 240, relative to the refillable tank portion 241, about a common longitudinal axis 260 (as shown in FIG. 2B).

After filling is complete, first and second fill apertures, respectively 259 and 254, may be misaligned by rotationally manipulating a mouthpiece portion 240 relative to a refillable tank portion 241 of the clearomizer 214. Once the fill apertures are misaligned, eCig juice is no longer able to flow into and out of refillable tank 250, and the user may resume regular operation of the eCig.

As discussed in more detail below, various embodiments of the present disclosure may utilize vent apertures that expedite filling of tank 250. The vent apertures, on both a refillable tank portion 241 and mouthpiece portion 240 of clearomizer 214, further facilitate filling of the refillable tank 250 with eCig juice by alleviating gas pressure build up as the tank fills with eCig juice. The vent apertures allow excess gas pressure to be quickly alleviated and thereby increase fill speed of the eCig juice. In one specific embodiment, the vent apertures exhaust gases from the refillable tank into a vapor chamber 255 within mouthpiece 240 and out of a plurality of nozzle apertures 256.

In various embodiments consistent with the present disclosure, mouthpiece 240 may include grip recesses $261_{A-F}$ which may extend into or protrude out of a portion of the mouthpiece 240. The grip recesses $261_{A-F}$ may take a number of shapes and sizes, with specific embodiments of the grip recesses $261_{A-F}$ being drawn to those best suiting functional aspects of the grip recesses $261_{A-F}$; for example, holding the mouthpiece 240 in a user's mouth. In many embodiments, the grip recesses $261_{A-F}$ may provide enhanced grip points between the user's teeth and the mouthpiece 240 of the eCig. Where multiple grip recesses $261_{A-F}$ are utilized, a user may adjust which grip recesses $261_{A-F}$ the user utilizes based on user preference, and/or comfort.

Figure 2D:
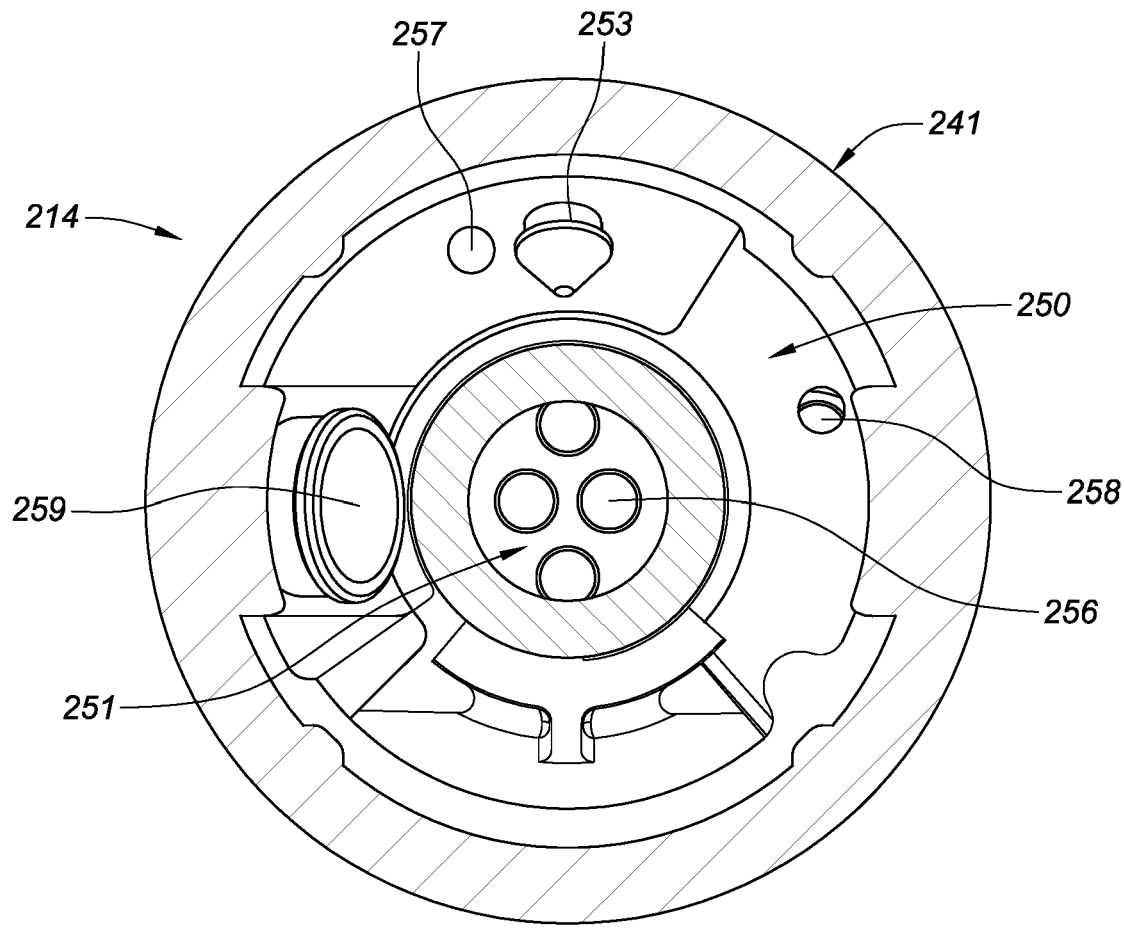
FIG. 2D is a cross-sectional view of the refillable eCig clearomizer taken along line B-B of FIG. 2B, consistent with various aspects of the present disclosure.

FIG. 2D is a cross-sectional back-side view of the refillable eCig clearomizer 214 of FIG. 2A, consistent with various aspects of the present disclosure. A central passage 251 delivers a flow of gas (including atomized eCig juice) from a heater coil within the clearomizer 214, through a plurality of nozzle apertures 256 in a nozzle of the clearomizer and to a user. Around a periphery of the central passage 251, a refillable tank 250 resides. The refillable tank 250 delivers eCig juice to a wick in fluid communication with the heater coil, and facilitates atomizing of the eCig juice in response to a user's draw on a mouthpiece.

When the eCig is in use, first fill aperture 259 and second fill aperture 254 (as shown in FIG. 2C) are misaligned; similarly, first vent aperture 257 and second vent aperture 258 are similarly misaligned to prevent the flow of eCig juice out of the refillable tank 250. A retention feature 253 is designed to locate and retain a seal that is located between the tank portion 241 and the mouthpiece portion 240.

During use, eCig juice within the refillable tank 250 is used, and the depletion of the juice within the refillable tank 250 may create a vacuum. In specific embodiments of the present disclosure, a pressure release valve may be implemented in the refillable tank 250 to relieve a vacuum state in the refillable tank. In one embodiment, the pressure release valve may align with a second fill aperture 254 (as shown in FIG. 2C) when the eCig is in use. In yet other embodiments, the pressure release valve may release a vacuum pressure regardless of orientation relative to the apertures on the mouthpiece 240. By releasing the vacuum pressure within the tank, the eCig will not experience performance degradation that is associated with a change in eCig juice level creating a vacuum pressure within the refillable tank 250; specifically, the pressure release valve may prevent performance degradation due to a decreased flow of eCig juice along a wick and into contact with the heater coil, which can be associated with a vacuum pressure within the refillable tank 250.

When the clearomizer requires eCig juice, first fill aperture 259 and second fill aperture 254 may be aligned to provide access to refillable tank 250. Similarly, first vent aperture 257 and second vent aperture 258 may be similarly aligned to facilitate the flow of eCig juice into the refillable tank 250 by alleviating a gas pressure build-up within the tank as eCig juice is added. The excess gas exhausts through the first and second vent apertures, into a vapor chamber 255, and out a plurality of nozzle apertures 256.

Various embodiments of the present disclosure are directed to an eCig clearomizer including a refillable tank and a mouthpiece. The refillable tank including a tank proximal portion and a tank distal portion, a first fill aperture, and a first annular channel around the proximal portion of the tank. The mouthpiece including a mouthpiece proximal portion and a mouthpiece distal portion, a second fill aperture, a first annular protuberance around the distal portion of the mouthpiece, wherein the first annular protuberance is slidably retained in the first annular channel to facilitate rotation of the mouthpiece relative to the refillable tank. In more specific embodiments, the refillable tank and the mouthpiece are rotatably coupled by the first annular channel and the first annular protuberance such that the mouthpiece may be rotated relative to the refillable tank about a common longitudinal axis.

In some embodiments, a refillable tank includes a first vent aperture, and a mouthpiece includes a second vent aperture. The mouthpiece may rotate relative to the refillable tank along a common longitudinal axis, and thereby align the first and second vent apertures concurrently with the alignment of the first and second fill apertures. In most embodiments, the fill and vent apertures facilitate filling of the refillable tank with the eCig juice, as well as preventing the flow of eCig juice out of the tank when the apertures are misaligned.

Rotatably aligned vent apertures of the refillable tank and the mouthpiece can also alleviate pressure build up in the refillable tank associated with filling the refillable tank with eCig juice.

In various embodiments of a clearomizer, a mouthpiece includes a nozzle, and an vapor chamber. The vapor chamber is located between the nozzle and the second vent aperture. In some embodiments, the rotatably aligned first and second vent apertures alleviate pressure build up in the refillable tank, associated with filling the refillable tank with eCig juice, by exhausting the pressurized gas through the first and second vent apertures, into the vapor chamber, and out the nozzle.

In various embodiments of a clearomizer consistent with the present disclosure, a refillable tank includes a pressure release valve. The pressure release valve and a first fill aperture of the refillable tank, when rotatably aligned, facilitate a release of a vacuum pressure within the refillable tank.

Aspects of the present disclosure are also directed toward an eCig clearomizer including a refillable tank, a heater coil, a wick, and a mouthpiece. The refillable tank contains eCig juice, which is drawn from the refillable tank to the heater coil by capillary action. The heater coil atomizes the juice in response to a current draw across the heater coil. The mouthpiece is coupled to a proximal portion of the refillable tank, and rotates relative to the refillable tank along a common longitudinal axis of the refillable tank and the mouthpiece.

In specific embodiments, a clearomizer includes complementary stopping features on both a mouthpiece and a refillable tank, the complementary stopping features limit the rotation of the refillable tank relative to the mouthpiece, along a common longitudinal axis. The complementary stopping features may also provide an audible indication and/or a tactile indication in response to reaching the rotational limit of the refillable tank relative to the mouthpiece.

In many embodiments of an eCig clearomizer consistent with the above, a refillable tank and a mouthpiece both include a fill aperture and a vent aperture, the fill and vent apertures can be rotatably aligned to facilitate filling of the refillable tank with eCig juice. In further embodiments, the rotatably aligned fill apertures of the refillable tank and the mouthpiece fluidly couple the refillable tank with an external environment for refilling the refillable tank with the eCig juice. The rotatably aligned vent apertures of the refillable tank and the mouthpiece may also alleviate pressure build up in the refillable tank associated with filling the refillable tank with the eCig juice. After filling, the fill and vent apertures can be rotatably mis-aligned to prevent escape of the eCig juice from within the refillable tank.

In various embodiments, a mouthpiece of a clearomizer includes a nozzle, and an vapor chamber. The vapor chamber is located between the nozzle and the mouthpiece vent aperture. When rotatably aligned, vent apertures of the refillable tank and the mouthpiece may alleviate pressure build up in the refillable tank, associated with filling the refillable tank with eCig juice, by exhausting pressurized gas through the vent apertures and the vapor chamber, and out the nozzle.

In some embodiments, a refillable tank includes a pressure release valve and a mouthpiece includes a fill aperture. The pressure release valve and the fill aperture can be rotatably aligned to release a vacuum pressure within the refillable tank.

In yet other embodiments, an eCig clearomizer is disclosed including a hemicylindrical port. The port includes a fluid inlet, and three electrical pads. At least one of the electrical pads are electrically coupled to a heater coil within the clearomizer, and the port electrically couples the heater coil with electrical circuitry of a power supply portion. The port also transfers a fluid from the power supply portion to the clearomizer in response to a draw via the fluid inlet. In one specific embodiment, the at least one of the electrical pads is electrically coupled to memory circuit within the clearomizer. In various embodiments, the three electrical pads are located on a flat surface of the hemicylindrical port. In more specific embodiments, the port can be mechanically and electrically coupled to a mating hemicylindrical port on a power supply portion of an eCig. In some specific embodiments, the hemicylindrical port is a male port and the mating hemicylindrical port is a female port.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the several views of the drawings.

The terms "including," "comprising" and variations thereof, as used in this disclosure, mean "including, but not limited to," unless expressly specified otherwise.

The terms "a," "an," and "the," as used in this disclosure, means "one or more," unless expressly specified otherwise.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

LIST OF REFERENCE SIGNS

10 electronic smoking device
12 end cap
14 power supply portion
16 atomizer/liquid reservoir portion
18 light-emitting diode (LED)
20 air inlets
22 battery
24 control electronics
26 airflow sensor
28 atomizer
30 heating coil
32 wick
34 central passage
36 liquid reservoir
38 air inhalation port 214 clearomizer
236 nozzle
240 mouthpiece
241 refillable tank portion
242 hemicylindrical port
243 window
244 filling port
245 electrical pads
250 refillable tank
251 central passage
252 interface
253 retention feature
254 second fill aperture
255 vapor chamber
256 nozzle aperture
257 first vent aperture
258 second vent aperture
259 first fill aperture
260 longitudinal axis
261 grip recess

What is claimed is:

1. An electronic cigarette cartomizer comprising:
    a hemicylindrical port;
    a refillable tank configured and arranged to contain electronic cigarette juice; and
    a vent aperture in fluid communication with the tank.

2. The cartomizer of claim 1, wherein the hemicylindrical port includes a fluid inlet, and electrical pads, at least one of the electrical pads are electrically coupled to a heater coil within the cartomizer.

3. The cartomizer of claim 2, wherein the hemicylindrical port is configured and arranged to
    electrically couple the heater coil with electrical circuitry of a power supply portion of an electronic cigarette, and
    transfer a fluid from the power supply portion to the cartomizer in response to a vacuum pressure within the cartomizer.

4. The cartomizer of claim 2, wherein the at least one of the electrical pads are electrically coupled to memory circuitry within the cartomizer.

5. The cartomizer of claim 2, wherein the electrical pads are located on a flat surface of the hemicylindrical port.

6. The cartomizer of claim 1, wherein the hemicylindrical port is further configured and arranged to be mechanically and electrically coupled to a mating hemicylindrical port on a power supply portion of an electronic cigarette.

7. The cartomizer of claim 1, further including
    a heater coil configured and arranged to atomize electronic cigarette juice in response to a current draw across the heater coil;
    a wick configured and arranged to draw the electronic cigarette juice from the refillable tank to the heater coil by capillary action; and
    a mouthpiece coupled to a proximal portion of the refillable tank.

8. The cartomizer of claim 7, wherein the refillable tank further includes a pressure release valve.

9. The cartomizer of claim 1, further including
    a heater coil configured and arranged to atomize electronic cigarette juice in response to a current draw across the heater coil; and
    a wick configured and arranged to draw the electronic cigarette juice from the tank to the heater coil by capillary action.

10. The cartomizer of claim 1, wherein the hemicylindrical port is configured and arranged to prevent relative rotation between the electronic cigarette cartomizer and a power supply portion coupled thereto, along a longitudinal axis.

11. An electronic cigarette cartomizer comprising:
    a hemicylindrical port;
    a refillable tank having a tank proximal portion, a tank distal portion, a first fill aperture, and a first annular channel around the proximal portion of the tank; and
    a mouthpiece having
        a mouthpiece proximal portion and a mouthpiece distal portion,
        a second fill aperture, and
        a first annular protuberance around the distal portion of the mouthpiece, wherein the first annular protuberance is slidably retained in the first annular channel to facilitate rotation of the mouthpiece relative to the refillable tank;
    wherein the refillable tank and the mouthpiece are thereby configured and arranged to permit relative rotation to selectably align and misalign the first and second fill apertures.

12. The cartomizer of claim 11, wherein the refillable tank and the mouthpiece are rotatably coupled by the first annular channel and the first annular protuberance such that the mouthpiece may be rotated relative to the refillable tank about a common longitudinal axis.

13. The cartomizer of claim 11, wherein the refillable tank includes a first vent aperture, and the mouthpiece includes a second vent aperture; the mouthpiece further configured and arranged to rotatably align the first and second vent apertures concurrently with the alignment of the first and second fill apertures.

14. The cartomizer of claim 13, wherein the fill and vent apertures are further configured and arranged to be rotatably misalignable to prevent escape of the electronic cigarette juice from within the refillable tank.

15. An electronic cigarette cartomizer comprising:
    a hemicylindrical port;
    a refillable tank configured and arranged to contain electronic cigarette juice;
    a heater coil configured and arranged to atomize electronic cigarette juice in response to a current draw across the heater coil;
    a wick configured and arranged to draw the electronic cigarette juice from the refillable tank to the heater coil by capillary action; and
    a mouthpiece coupled to a proximal portion of the refillable tank, the mouthpiece including a nozzle, a vapor chamber, and a vent aperture, wherein the vent aperture is in fluid communication with the refillable tank.

16. The electronic cigarette cartomizer of claim 15, wherein the vent aperture is not in fluid communication with the vapor chamber or the nozzle.

17. The electronic cigarette cartomizer of claim 15, wherein the vent aperture is configured and arranged to return the refillable tank to atmospheric equilibrium in response to partially filing the refillable tank with electronic cigarette juice.

* * * * *